(12) United States Patent
Arghyris et al.

(10) Patent No.: US 6,261,274 B1
(45) Date of Patent: Jul. 17, 2001

(54) DEVICE FOR DISPENSING A FLUID OR A POWDER AT A PREDETERMINED DISTANCE

(75) Inventors: Laurent Arghyris, Sotteville-les-Rouen; Michel Bedos, Viols-le-Fort, both of (FR)

(73) Assignee: Valois S.A., Le Nebourg (FR)

( * ) Notice: Subject to any disclaimer, the term of this patent is extended or adjusted under 35 U.S.C. 154(b) by 0 days.

(21) Appl. No.: 09/341,823

(22) PCT Filed: Jan. 19, 1998

(86) PCT No.: PCT/FR98/00087

§ 371 Date: Oct. 4, 1999

§ 102(e) Date: Oct. 4, 1999

(87) PCT Pub. No.: WO98/31412

PCT Pub. Date: Jul. 23, 1998

(30) Foreign Application Priority Data

Jan. 20, 1997 (FR) .................................................. 97/00541

(51) Int. Cl.[7] .................................................. A61M 35/00

(52) U.S. Cl. .......................................................... 604/289

(58) Field of Search ................................... 604/289, 294, 604/295, 290, 300, 301, 302; 128/200.14, 200.23

(56) References Cited

U.S. PATENT DOCUMENTS 4,296,317  10/1981  Kraus .
5,588,564  12/1996  Hutson et al. .

FOREIGN PATENT DOCUMENTS

2682305  *  4/1993  (FR) .
2 000 555     1/1979  (GB) .

* cited by examiner

Primary Examiner—Kim M. Lewis
(74) Attorney, Agent, or Firm—Sughrue, Mion, Zinn, Macpeak & Seas, PLLC

(57) ABSTRACT

A device for spraying or dispensing a fluid or powdery product on a surface to be treated and/or an intake element (50), comprising: a dispensing member (1), including a dispensing opening (31), the dispensing member being associated with a reservoir (2) containing the product and being movable between an inoperative position and a dispensing position; and an actuating device for moving the dispensing member (1) towards its dispensing position for delivering a dose of product: The device further comprises: a device for measuring distance (20) movable between an inoperative position and their useful position, and arranged in their useful position such that each time the device is used the dispensing opening (31) is located at a fixed predetermined distance from the surface to be treated and/or the intake element (50), the movement of the distance measuring device (20) from their useful position towards their inoperative position bringing the dispensing member (1) back towards its inoperative position.

15 Claims, 4 Drawing Sheets

DEVICE FOR DISPENSING A FLUID OR A POWDER AT A PREDETERMINED DISTANCE

CROSS REFERENCE TO RELATED APPLICATIONS

This application is a §371 application of PCT/FR98/00087 filed Jan. 19, 1998.

BACKGROUND OF THE INVENTION

1. Field of the Invention

The present invention relates to a device for dispensing a fluid or a powder, and more particularly it relates to such a device provided with means enabling it to be used at a determined distance from the location to be treated.

2. Description of the Relate Art

A mechanically-actuated device for spraying or dispensing a fluid is known from document FR-2 682 305. In that device, a pump is cocked by means of an actuator spring, the device including spring-locking means, trigger means, and a cap for protecting the housing and provided with means for re-cocking the device, which means become operative while said cap is being closed.

Because it is triggered independently of the user, that prior device operates in satisfactory manner, in particular by guaranteeing that reproducible quantities are dispensed, however it does not make it possible to comply with certain requirements that can arise as a function of the type of substance to be dispensed and the type of use to which the device is put.

Thus, for certain substances, e.g. substances for systemic use such as hormone replacement therapy, the area to be sprayed must be defined as accurately as possible in order to make bioavailability reproducible. In particular, for transdermal use, it is important to distribute the sprayed liquid over an area that is predetermined, reproducible, and uniform, in order to favor reproducible absorption by the skin.

Also, in ophthalmological use, in order to promote compliance, it is important to ensure that the substance, e.g. a drop of liquid, reaches the eye under the same dynamic conditions.

In addition, for pulmonary use, in order to reduce side-effects, it can sometimes be important to ensure that sprayed particles of small size only are breathed in by the patient, and to avoid any large particles (which cannot be inhaled because of their size) becoming deposited in the patient's mouth, where they could generate undesirable effects, such as candidosis, for example. For this purpose, it is necessary to spray from a distance that is large enough to ensure that heavy large particles do not reach the mouth, while being small enough to ensure that small particles are breathed in.

BRIEF SUMMARY OF THE INVENTION

An object of the present invention is to provide a dispenser device which satisfies the above-specified requirements and which does not have the above-mentioned drawbacks. In particular, an object of the present invention is to provide a dispenser device with which the effectiveness and/or the therapeutic benefit of the dispensed substance is maximal.

Another object of the present invention is to provide a dispenser device which simultaneously guarantees reproducibility of the dose, reproducibility of the area to be treated, and reproducibility of the dynamics of the dispensed substance, i.e. which guarantees reproducibility of the action and the effectiveness of the substance on the patient.

A further object of the present invention is to provide such a device which promotes compliance and/or optimizes bio-availability and/or reduces side-effects.

A further object of the present invention is to provide such a device which is simple to make and to use, and which in particular ensures maximum efficiency for the user on each actuation.

The present invention thus provides a device for dispensing a fluid or a powder onto a surface to be treated and/or into an organ presenting an entrance, the device comprising:

a dispenser member having a dispenser orifice, said dispenser member being associated with a reservoir containing the substance to be dispensed and being movable between a rest position and a dispensing position; and actuator means for moving said dispenser member towards its dispensing position to dispense a dose of substance;

the device being characterized in that it further comprises:

distance-gauging means movable between a rest position and an in-use position, and being disposed in the in-use position in such a manner that on each use of the device, the dispenser orifice is situated at a predetermined fixed distance from the surface to be treated and/or from the organ presenting an entrance, the act of moving said distance-gauging means from their in-use position to their rest position causing said dispenser member to be returned from its dispensing position to its rest position.

Preferably, said actuator means comprise resilient means acting on the dispenser member while it is in the rest position, urging it towards the dispensing position in which it dispenses a measured quantity of the substance in full, locking means for locking said resilient means to hold the dispenser member in its rest position, and trigger means actuatable by the user to release said locking means and thereby bring the dispenser member towards its dispensing position. Thus, triggering and dispensing of the measured quantity are independent of the actuation force, and reproducibility is guaranteed, even if the user is very weak.

Advantageously, said distance-gauging means include re-cocking means which, when said distance-gauging means are returned from the in-use position to the rest position, act on the dispenser member to return it to its own rest position against the force of the resilient means, after which said resilient means are locked by said locking means.

Advantageously, said distance-gauging means are implemented in the form of a sheath including a cap, said cap closing the dispenser orifice of the dispenser member and said sheath covering said trigger means, thereby preventing the device from being actuated while said distance-gauging means are in the rest position. The device of the invention thus also makes it possible to protect the dispenser orifice during storage, e.g. against dust, and to prevent undesired actuation of the device.

Preferably, said distance-gauge means are permanently connected to said device, movement of said distance-gauging means between the rest position and the in-use position being constituted by a translation movement parallel to the central axis of the device and a rotation movement about an axis perpendicular to the central axis of the device, said re-cocking means acting during said translation movement while the distance-gauging means are being returned to the rest position.

Advantageously, said distance-gauging means include two arms connected to the body of the device, said arms sliding in two grooves provided in said body, said two arms also being capable of pivoting through about 90° about an axis of rotation extending transversely to the central axis of the device level with the top ends of the two grooves.

Preferably, the device includes a nozzle upstream from said dispenser orifice, thereby defining the spatial configuration with which the measured quantity of substance is sprayed. This makes it possible to predetermine the area to be treated even better, and to reproduce it exactly on each actuation.

Advantageously, the surface to be treated and/or the organ presenting an entrance is a portion of the human body.

Advantageously, the dispenser member is a pump.

Advantageously, the dispenser member is a metering valve.

Advantageously, the resilient means are implemented in the form of a spring.

In an advantageous embodiment, the dispenser device is a powder dispenser, such as an active or a passive inhaler. Naturally, any other type of powder dispenser can be envisaged.

In an advantageous embodiment of the invention, said distance-gauging means are adapted to press against the body of the patient in the vicinity of said surface to be treated, the substance acting in transdermal manner and/or in systemic manner on said surface to be treated.

Advantageously, the substance includes replacement hormones.

Advantageously, the substance includes estrogens.

In another advantageous embodiment of the invention, the substance is a liquid, the surface to be treated is an eye, and said distance-gauging means are adapted to press beneath or around said eye.

In yet another advantageous embodiment of the invention, said distance-gauging means are adapted to press on or around the mouth of the user, the substance being dispensed inside said distance-gauging means, the length of said distance-gauging means being selected in such a manner that only finely-divided particles of substance reach the mouth, with larger particles falling under the effect of their own weight inside said distance-gauging means before reaching the mouth.

BRIEF DESCRIPTION OF THE DRAWINGS

Other characteristics and advantages appear from the following detailed description of an embodiment of the invention given by way of non-limiting example and described with reference to the accompanying drawings, in which.

DETAILED DESCRIPTION OF THE INVENTION

The present invention applies to any device for spraying or dispensing a fluid or a powder and including a dispenser member such as a pump or a metering valve associated with a reservoir containing the substance, said dispenser member including a dispenser orifice. The device also includes means for actuating said disperser member to dispense one measured quantity or "dose" of substance, and, in accordance with the invention, distance-gauging means which, in their in-use position, are disposed in such a manner as to define, on each use of the device, a fixed predetermined distance between the dispenser orifice and the surface to be treated and/or an organ presenting an entrance.

The surface to be treated can be any portion, in particular of a human body, suitable for receiving the sprayed substance, and in particular zones of the skin, the mouth, the nose, the eyes, or the lungs of the user. The term "organ presenting an entrance" is used to cover any opening in the human body against which the distance-gauge means can be pressed when the substance is for an internal portion of the body. Thus, for example, when the area to be treated is constituted by the lungs, then the mouth is used as an organ presenting an entrance.

Although the invention is of general applicability, it is described below with reference to a particular embodiment in which the invention constitutes an improvement over the spray device disclosed in document FR-2 682 305. Document FR-2 682 305 is thus incorporated in the present description by way of reference, particularly concerning the general operation of the device, and specifically the way in which it is triggered independently of the actuation force.

Figure 1:
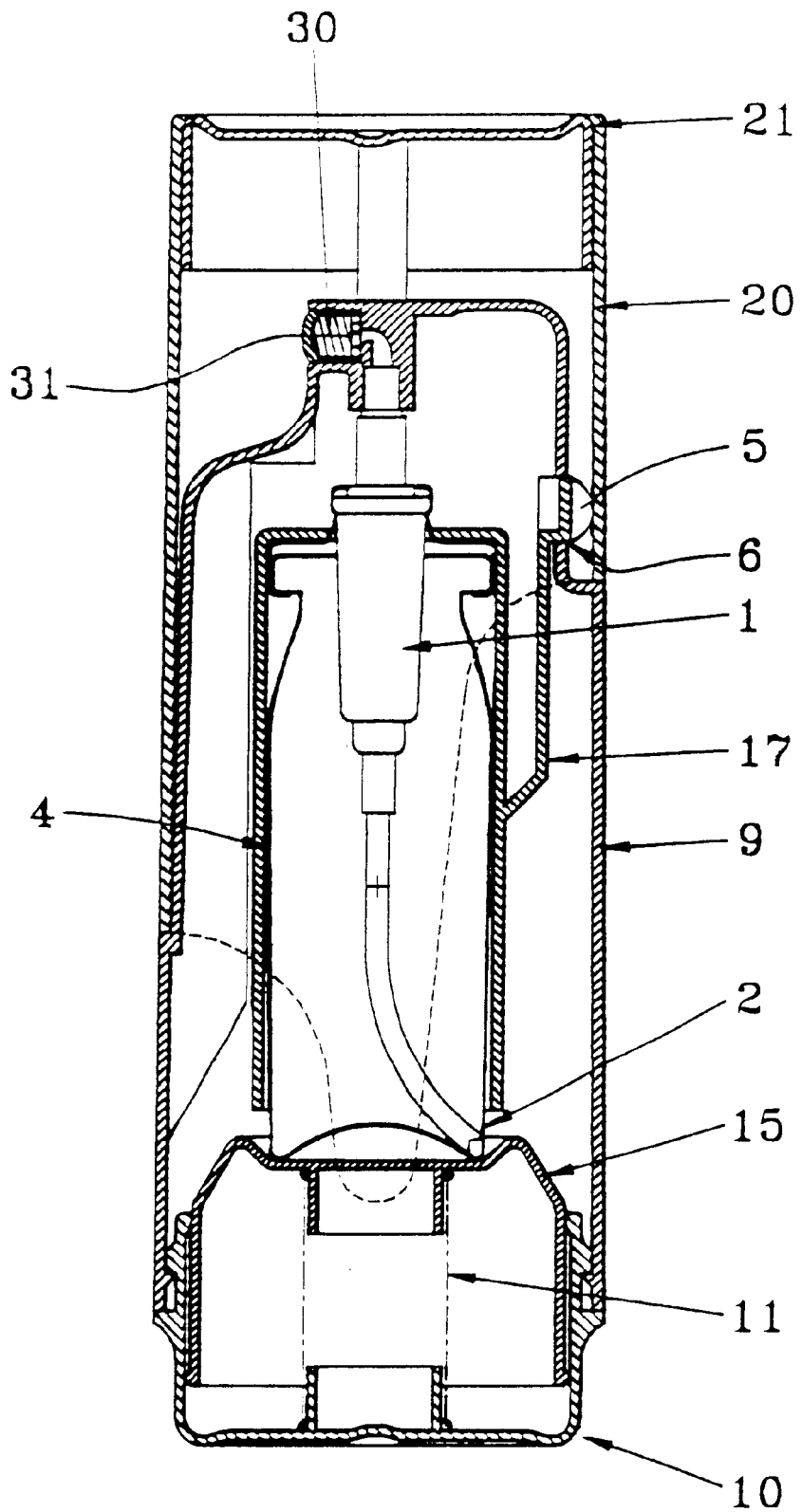
FIG. 1 is a diagrammatic section view of a particular embodiment of the invention shown with the device having its cap in the closed state.
Figure 2:
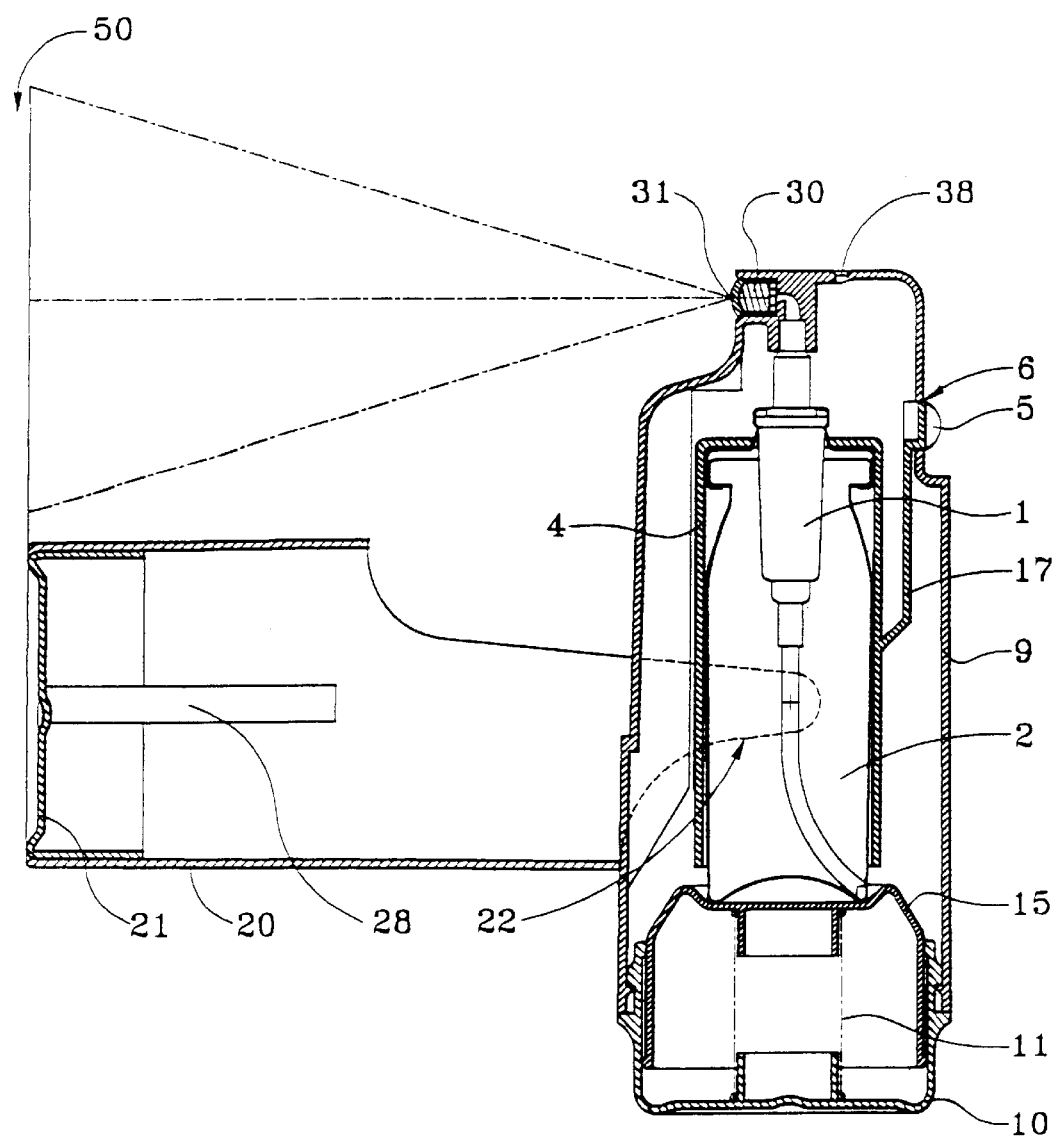
FIG. 2 is a diagrammatic section view of the FIG. 1 device with its cap in the in-use position.

With reference to FIGS. 1 and 2, the device comprises a pump 1 mounted on a reservoir 2 and disposed inside a case 4, said pump 1 being movable between a rest position and a dispensing position in which it dispenses a dose of substance. To do this, it includes actuator means, preferably mechanical actuator means, which include resilient means such as a spring 11 acting on the pump 1 when in its rest position to urge it towards its dispensing position, locking means 5, 6 which lock said resilient means 11 and hold the dispenser member 1, i.e. the pump 1, in its rest position, and trigger means, 5, 17 for releasing said locking means. Thus, when the user actuates said trigger means 5, 17, the pump 1 is moved by the spring 11 towards its dispensing position where it dispenses a dose of substance through its dispenser orifice 31.

The spring is preferably disposed between a bottom endpiece 10 fixed to the body 9 of the device and a moving support element 15 which supports the reservoir 2. Thus, when the trigger means are actuated by the user, the support element 15 drives the reservoir, the case 4, and the pump 1 causing them to move upwards in the figures under drive from the spring 11, thereby actuating the pump.

As shown in FIGS. 1 and 2, the locking and trigger means advantageously include a catch 5 which snaps into an opening 6 secured to the body 9, the catch 5 being secured to a resilient arm 17 fixed to said case 4 surrounding the reservoir 2 and the pump 1. Said catch 5 is thus urged by the resilient arm 17 towards its snap-fastened position where it locks the spring 11.

In accordance with the invention, the device includes distance-gauging means 20 which, in the in-use position, serve to determine and fix the distance between the dispenser orifice 31 and the zone to be treated and/or the organ presenting an entrance 50. Preferably, and as shown in the figures, the distance-gauging means 20 are formed by the sheath 20 fitted with the cap 21 as disclosed in document FR-2 682 305. Thus, in the rest position, said distance-gauging means close said dispenser orifice 31 of the pump 1, thereby protecting it, e.g. against dust, and also advantageously covering the trigger catch 5, thus preventing any unwanted or untimely actuation of the dispenser. To be able to use the dispenser, it is therefore necessary to withdraw said distance-gauging means 20. To do this, the sheath 20 must advantageously perform firstly a movement in translation followed by a movement in rotation. Thus, and as can be seen in particular in FIG. 3, the sheath 20 has two arms 22 which are permanently connected to the body 9 of the dispenser, said arms 22 sliding in translation in corresponding grooves 25 formed in the body 9, such that when it is desired to use the device, the sheath 20 is initially lifted in translation parallel to the central axis of the dispenser, and then caused to pivot, advantageously through 90°, about an axis extending transversely to said central axis of the dispenser. This leads to the position shown in FIGS. 2 and 3. Similarly, after the dispenser has been used, the sheath 20 is advantageously pivoted initially about its axis of rotation, and then pushed in a direction parallel to the central axis of the dispenser so as to cause the arms 22 to slide back along the grooves 25. During this movement in translation, re-cocking means 28 provided in the sheath 20 passing through one or more openings 38 in the body 9 co-operate with the case 4 to move it towards the rest position of the pump 1 against the force of the spring 11. Once the pump has been returned to its rest position, the spring 11 is compressed while the catch 5 under the effect of the resilience of the resilient arm 17 is snapped into the opening 6 in the body 9 to lock the pump in its rest position. The device is then ready to be used again.

It should be understood that the invention is not limited to the embodiment described above and that on the contrary the invention applies to any type of dispenser that includes a prestressed pump and distance-gauging means that also serve to re-cock the pump. The distance-gauging means may be displaced relative to the device in any appropriate manner providing it serves, when the device is in use, to define a reproducible surface area to be treated, guaranteeing on each occasion that there is the same distance between the dispenser orifice and the surface to be treated and/or the organ presenting an entrance. In addition, in accordance with the invention, said distance-gauging means also serve, while they are being returned to the rest position, to re-cock the pump or its actuator device, as described above with reference to an advantageous embodiment.

Preferably, the device further includes a nozzle 30 disposed close to the dispenser orifice 31 and designed to configure, in reproducible manner, the way in which the dose of substance is sprayed. Thus, in combination with a fixed spraying distance, the device of the invention also makes it possible to obtain a fixed and reproducible distribution of the dose of substance over the surface to be treated and/or the organ presenting an entrance.

Figure 3:
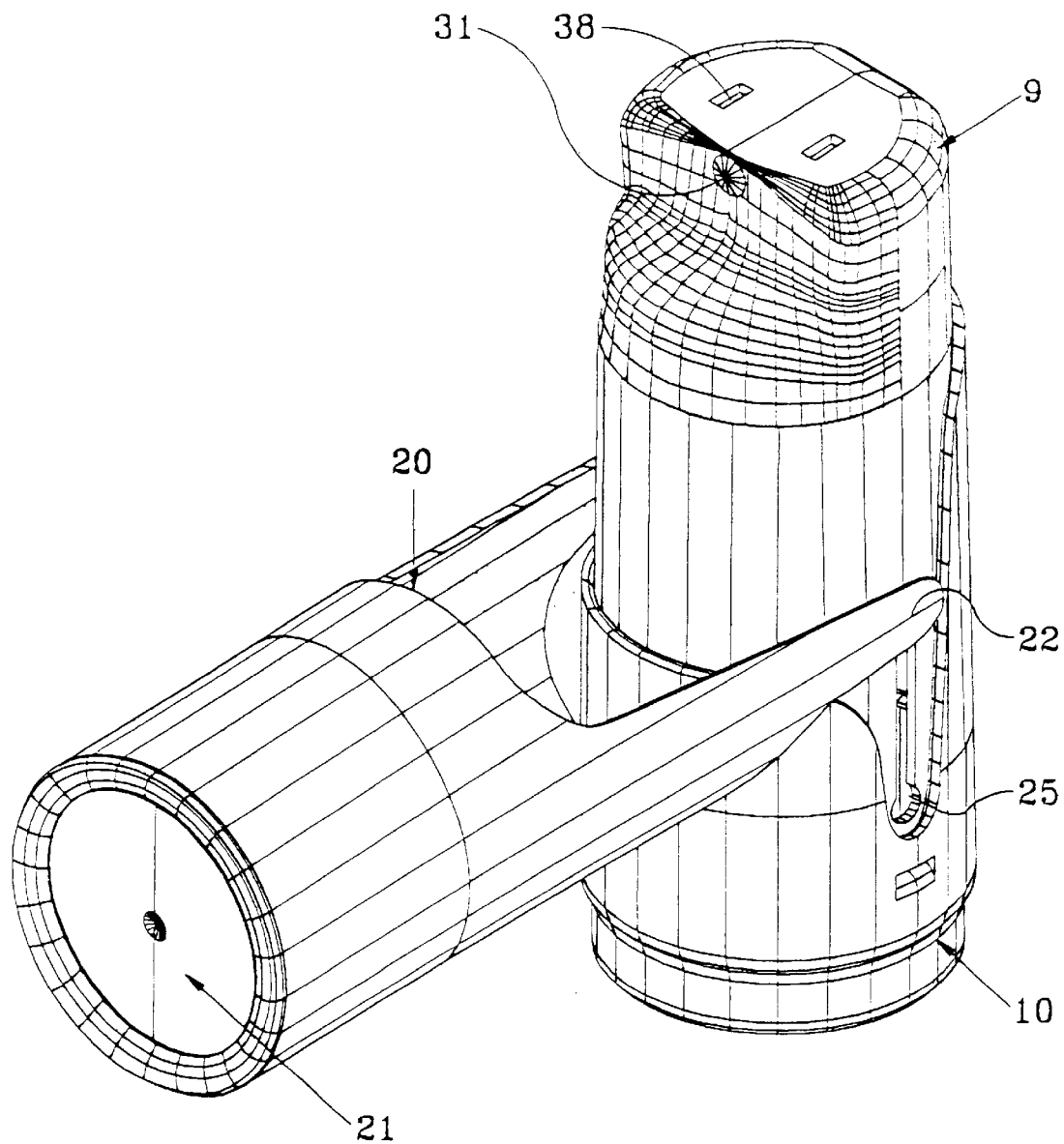
FIG. 3 is a diagrammatic perspective view of a device constituting a particular embodiment of the invention, shown with its cap in the in-use position.

The device shown diagrammatically in FIGS. 1, 2, and 3 is particularly designed for transdermal use, where a suitable substance is to be dispensed over a surface to be treated that corresponds to a portion of the skin of the patient. In this use, the distance-gauging means 20 are pressed against the body of the patient in the vicinity of said surface to be treated 50 so as to determine in precise manner the distance between the dispenser orifice 31 and said surface to be treated, thereby obtaining an area to be treated 50 that is reproducible in the intended manner. Under such circumstances, the substance can be for hormone replacement therapy, e.g. being constituted of estrogens.

Figure 4A:
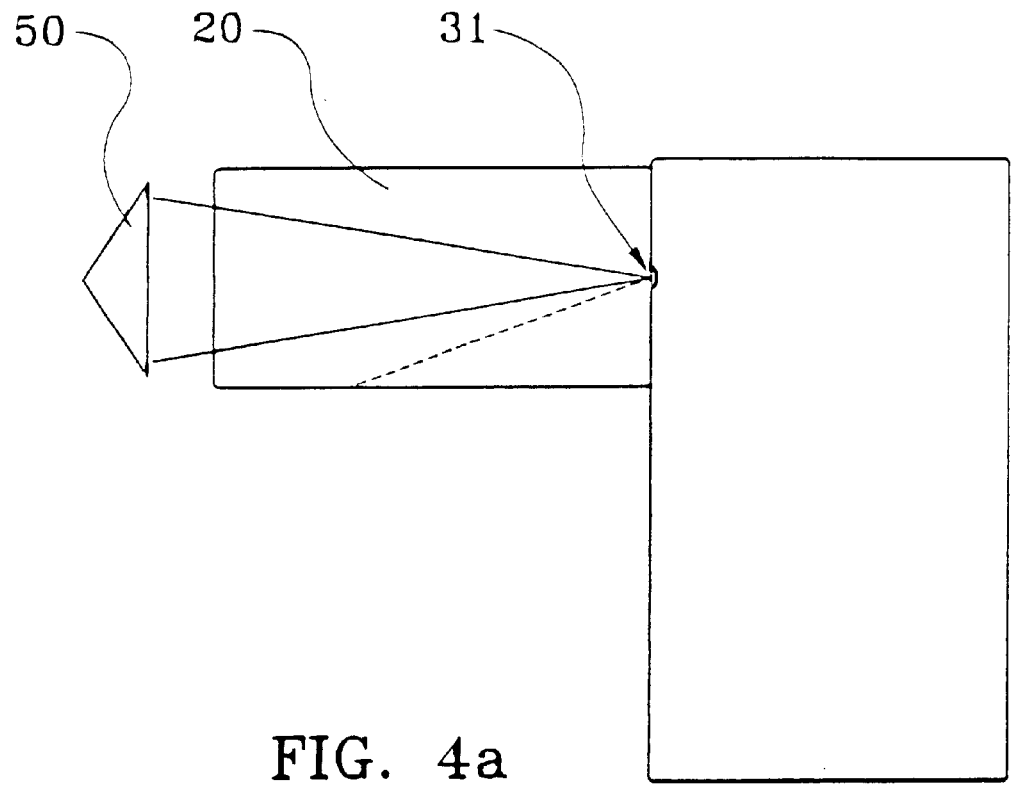
FIGS. 4a and 4b are diagrams showing two variant uses of the device of the invention.
Figure 4B:
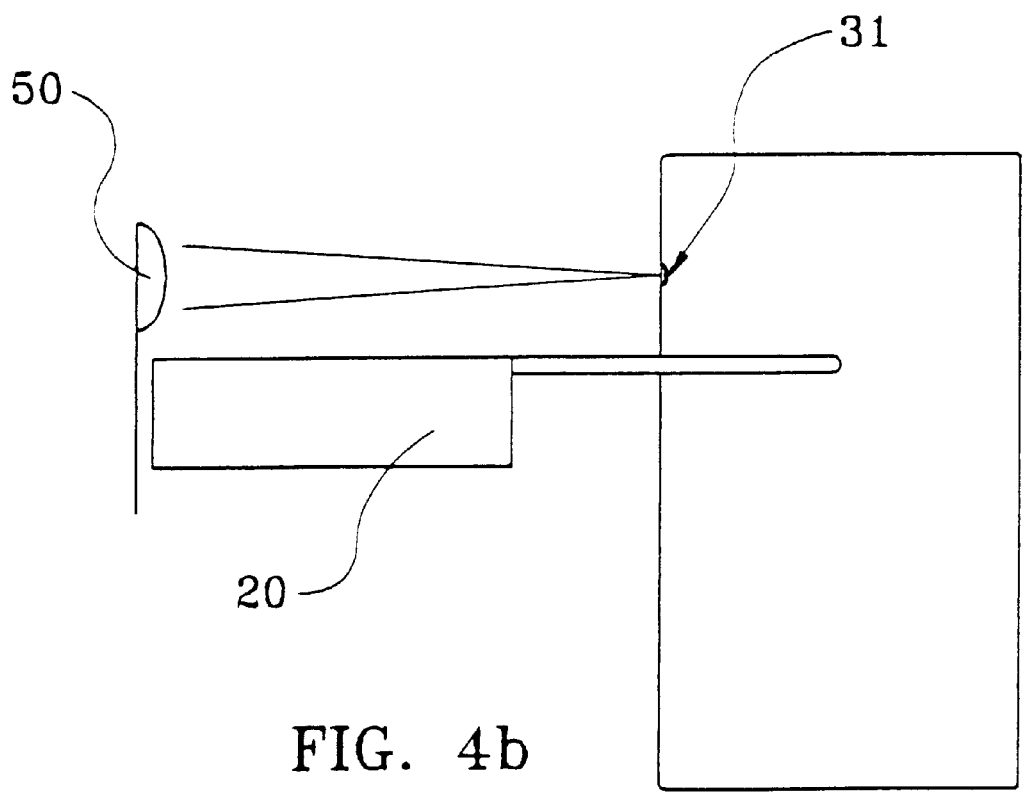

FIGS. 4a and 4b are highly diagrammatic and show two other possible uses for the device of the invention. Thus, with reference to FIG. 4b, the device can be used in ophthalmology for dispensing a liquid into an eye 50. Under such circumstances, said distance-gauging means 20 are preferably pressed either beneath or around said eye 50.

In FIG. 4a, the device of the invention is used to dispense a liquid or a powder into the lungs of the user. In this case, the distance-gauging means 20 press against the organ presenting an entrance, i.e. the mouth 50 of the user. Thus, in this use, the substance is dispensed inside said distance-gauging means 20, with the length of said distance-gauging means being selected in such a manner that only finely divided particles of the substance reach the mouth 50, thereby making it possible to eliminate. larger particles which, under the effect of their own weight, fall inside said distance-gauging means 20 before reaching the mouth 50. This is represented in FIG. 4a by the dashed line.

Naturally, variant embodiments of the device of the invention can be used, providing they perform the same above-mentioned functions in each case.

The device of the invention thus makes it possible to satisfy the above-mentioned requirements in optimal manner. Thus, when the device is used in ophthalmology, the distance gauge which is placed beneath or around the eye to be treated guarantees proper operation of the device and ensures that the drop does indeed reach the eye, thus favoring observance. Also, with transdermal use, the distance gauge makes it possible to optimize bioavailability by always positioning the device at the same distance from the skin, such that a uniform and reproducible treated area is obtained. In addition, when used for the lungs, the distance gauge makes it possible, in particular, to reduce side effects by serving to trap large particles and allowing only small particles to escape.

What is claimed is:

1. The device for dispensing a substance onto a surface to be treated and/or into an organ presenting an entrance (50), the device comprising:

a dispenser member (1) having a dispenser orifice (31), said dispenser member being associated with a reservoir (2) containing the substance to be dispensed and being movable between a rest position and a dispensing position;

actuator means (5, 6, 11, 17) for moving said dispenser member (1) towards its dispensing position to dispense a dose of the substance; and distance-gauging means (20) movable between a rest position in which said distance-gauging means (20) prevents actuation of said dispenser member (1), and an in-use position in which said distance-gauging means (20) cooperates with the surface to be treated and/or the organ presenting an entrance (50) such that the dispenser orifice (31) is situated at a predetermined fixed distance from said surface to be treated and/or from said organ presenting an entrance (50), wherein the act of moving said distance-gauging means (20) from its in-use position to its rest position, after actuation of the dispenser member (1), causes said dispenser member (1) to be returned from its dispensing position to its rest position.

2. The device according to claim 1, wherein said actuator means comprise resilient means (11) acting on the dispenser member (1) while it is in the rest position, urging it towards the dispensing position in which it dispenses a measured quantity of the substance, locking means (5, 6) for locking said resilient means to hold the dispenser member in its rest position, and trigger means (5, 17) actuatable by a user to release said locking means and thereby bring the dispenser member towards its dispensing position.

3. The device according to claim 2, wherein said distance-gauging means 20) include re-cocking means (28) which, when sad stance-gauging means 20) is returned from the in-use position to the rest position, act on the dispenser member (1) to return it to its rest position against the force of the resilient means (11), after which said resilient means (11) is locked by said locking means (5, 6).

4. The device according to claim 3, wherein said distance-gauging means (20) is implemented in the form of a sheath (20) including a cap (21), said cap (21), in the rest position, closing the dispenser orifice (31) of the dispenser member (1) and said sheath (20), in the rest position, covering said trigger means (5), thereby preventing the device from being actuated.

5. The device according to claim 3, wherein said distance-gauge means (20) is permanently connected to said device, movement of said distance-gauging means (20) between the rest position and the in-use position being constituted by a translation movement parallel to the central axis of the device and a rotation movement about an axis perpendicular to the central axis of the device, said re-cocking means (28) acting during said translation movement while the distance-gauging means (20) is being returned to the rest position.

6. The device according to claim 5, wherein said device comprises a body (9), said distance-gauging means (20) including two arms (22) connected to the body (9) of the device, said arms (22) sliding in two grooves (25) provided in said body (9), said two arms (22) also being capable of pivoting through about 90° about an axis of rotation extending transversely to the central axis of the device level with the top ends of the two grooves (25).

7. The device according to claim 1, including a nozzle (30) upstream from said dispenser orifice (31), thereby defining the spatial configuration with which the dose of substance is sprayed.

8. The device according to claim 1, wherein the surface to be treated and/or the organ presenting an entrance (50) is a portion of the human body.

9. The device according to claim 1, wherein the dispenser member (1) is a pump.

10. The device according to claim 1, wherein the dispenser member (1) is a metering valve.

11. The device according to claim 1, wherein the resilient means (11) is implemented in the form of a spring.

12. The device according to claim 1, wherein the dispenser device is a powder dispenser.

13. The device according to claim 1, wherein said distance-gauging means (20) is adapted to press against the body of the patient in the vicinity of said surface to be treated (50).

14. The device according to claim 1, wherein the dispensing device is a liquid dispenser, the surface to be treated (50) is an eye, and said distance-gauging means (20) is adapted to press beneath or around the eye (50).

15. The device according to claim 1, wherein said distance-gauging means (20) is adapted to press on or around the mouth (50) of the user, the substance being dispensed inside said distance-gauging means (20), the length of said distance-gauging means (20) being selected in such a manner that only finely-divided particles of substance reach the mouth (50), with larger particles falling under the effect of their own weight inside said distance-gauging means (20) before reaching the mouth.

* * * * *

UNITED STATES PATENT AND TRADEMARK OFFICE
CERTIFICATE OF CORRECTION

PATENT NO. : 6,261,274 B1  Page 1 of 1
DATED : July 17, 2001
INVENTOR(S) : Laurent Arghyis and Michael Bedos It is certified that error appears in the above-identified patent and that said Letters Patent is hereby corrected as shown below:

<u>Title page,</u>
Item [73], Assignee, please delete "Valois S.A., Le Nebourg (FR)" and insert
-- Valois S.A., Le Neubourg (FR) and Sanofi-Synthelabo, Paris (FR) --

Signed and Sealed this

Sixteenth Day of December, 2003

JAMES E. ROGAN
*Director of the United States Patent and Trademark Office*